US011478494B2

(12) United States Patent
Farmer et al.

(10) Patent No.: US 11,478,494 B2
(45) Date of Patent: Oct. 25, 2022

(54) METHODS AND SUBSTANCES FOR PREVENTION AND TREATMENT OF NEURODEGENERATIVE DISEASES

(71) Applicant: Locus IP Company, LLC, Solon, OH (US)

(72) Inventors: Sean Farmer, North Miami Beach, FL (US); Ken Alibek, Solon, OH (US); Alibek Moldakozhayev, Solon, OH (US); Albina Tskhay, Solon, OH (US)

(73) Assignee: LOCUS IP COMPANY, LLC, Solon, OH (US)

( * ) Notice: Subject to any disclaimer, the term of this patent is extended or adjusted under 35 U.S.C. 154(b) by 0 days.

(21) Appl. No.: 16/754,426

(22) PCT Filed: Oct. 15, 2018

(86) PCT No.: PCT/US2018/055861
§ 371 (c)(1),
(2) Date: Apr. 8, 2020

(87) PCT Pub. No.: WO2019/075456
PCT Pub. Date: Apr. 18, 2019

(65) Prior Publication Data
US 2020/0338106 A1  Oct. 29, 2020

Related U.S. Application Data

(60) Provisional application No. 62/572,145, filed on Oct. 13, 2017.

(51) Int. Cl.
*A61K 31/7048* (2006.01)
*A61K 9/00* (2006.01)

(52) U.S. Cl.
CPC ........ *A61K 31/7048* (2013.01); *A61K 9/0053* (2013.01)

(58) Field of Classification Search
CPC .......................... A61K 31/7048; A61K 9/0053
USPC ....................................................... 514/27
See application file for complete search history.

(56) References Cited

U.S. PATENT DOCUMENTS

| | | |
|---|---|---|
| 6,955,873 B1 | 10/2005 | Blum |
| 2007/0280911 A1 | 12/2007 | Cobb et al. |
| 2010/0234385 A1 | 9/2010 | Hasegawa et al. |
| 2010/0267684 A1 | 10/2010 | Seong et al. |
| 2011/0091431 A1 | 4/2011 | Olmstead |
| 2011/0183019 A1 | 7/2011 | Theoharides |
| 2012/0142621 A1* | 6/2012 | Falus ................ A61K 31/7028 514/31 |
| 2014/0187507 A1* | 7/2014 | DeFrees ............ A61K 31/7042 514/32 |
| 2015/0037302 A1 | 2/2015 | Bralkowski et al. |
| 2015/0045290 A1 | 2/2015 | Coutte et al. |
| 2015/0258164 A1 | 9/2015 | Murdock et al. |
| 2016/0083757 A1 | 3/2016 | Fonseca et al. |
| 2016/0369357 A1 | 12/2016 | Taylor |

FOREIGN PATENT DOCUMENTS

| | | |
|---|---|---|
| CN | 106389479 A | 2/2017 |
| EP | 0540074 A1 | 5/1993 |
| WO | 2008140262 A2 | 11/2008 |
| WO | 2014046700 A1 | 3/2014 |
| WO | 2016168197 A1 | 10/2016 |
| WO | 2017007099 A1 | 1/2017 |

OTHER PUBLICATIONS

McCoy et al. (Journal of Neuroinflammation 2008, 5:45, 1-13).*
Morita et al. (Biochimica et Biophysica Acta 1810 (2011) 1302-1308).*
Andreadou, E., et al., "Rhamnolipids, Microbial Virulence Factors, in Alzheimer's Disease." Journal of Alzheimer's Disease, 2017, 59: 209-222.
De Brito, D., Biosurfactants from renewable raw materials, Universidade do Minho Departamento de Engenharia Biologica, Nov. 2013, pp. 1-93.
De Oliveira, M., et al., "Review: Sophorolipids a Promising Biosurfactant and it's Applications." International Journal of Advanced Biotechnology and Research, 2015, 6(2): 161-174.
Hill, J.M., et al., "The gastiointestinal tract microbiome and potential link to Alzheimer's disease." Frontiers in Neurology, 2014, 5(43): 1-4.
Kurtzman, C.P., et al., "Production of sophorolipid biosurfactants by multiple species of the *Starmerella* (Candida) bombicolayeast clade." FEMS Microbiol Lett, 2010, 311: 140-146.
Nitschke, M., et al., "Production and properties of a surfactant obtained from Bacillus subtilis grown on cassava wastewater." Bioresouice Technology, 2006, 97: 336-341.
Sen, R., "Biosurfactants: Advances in Experimental Medicine and Biology." Landes Bioscience and Springer Science+Business Media, LLC, 2010, 672: 1-331.
Sharma, A. et al., "A study on biosurfactant production in *Lactobacillus* and *Bacillus* sp." Int. J. Curr. Microbiol. App. Sci., 2014, 3(11): 723-733.
Sil, J., et al., "Health Care Applications of Different Biosurfactants: Review." International Journal of Science and Research (IJSR), 2015, 6(10): 41-50.
Park, S.Y., et al., "Surfactin exhibits neuroprotective effects by inhibiting amyloid β-mediated microglial activation." NeuroToxicology, 2013, 38: 115-123.

(Continued)

*Primary Examiner* — Shaojia A Jiang
*Assistant Examiner* — Michael C Henry
(74) *Attorney, Agent, or Firm* — Saliwanchik, Lloyd & Eisenschenk

(57) ABSTRACT

The present invention provides compositions and methods for the treatment of neurological disorders. In particular, the present invention can be used for treating and/or preventing the symptoms and/or comorbidities of neurodegenerative conditions, diseases or disorders, such as, for example, Alzheimer's and Parkinson's disease.

12 Claims, No Drawings

(56) References Cited

OTHER PUBLICATIONS

Park, S.Y., et al., "Involvement of PKA and HO-1 signaling in anti-inflammatory effects of surfactin in BV-2 microglial cells." Toxicology and Applied Pharmacology, 2013, 268: 68-78.

* cited by examiner

METHODS AND SUBSTANCES FOR PREVENTION AND TREATMENT OF NEURODEGENERATIVE DISEASES

CROSS-REFERENCE TO RELATED APPLICATION

This application is a National Stage Application of International Application No. PCT/US2018/055861, filed Oct. 15, 2018; which claims priority to U.S. Provisional Patent Application No. 62/572,145, filed Oct. 13, 2017, both of which are incorporated by reference herein in their entirety.

BACKGROUND OF INVENTION

Neurodegeneration is the progressive pathologic loss of structure or function of neurons, which can be followed by their death. Most neurodegenerative diseases, including, for example, Alzheimer's disease and Parkinson's disease, occur as a result of neurodegenerative processes.

The causes of many neurological diseases remain disputed; however, it is now accepted that the immune protection of the brain is not absolute and that cells of the central nervous system are sensitive to infections capable of penetrating the blood-brain barrier, to inflammatory events occurring in the periphery, and to the infiltration of peripheral immune cells. Genetic relationships have been found in neurodegenerative diseases, but the changes in the expression of genes are usually not directly related to simple genetic changes.

Neurodegenerative mental diseases have many signs of molecular and genetic changes in nerve cells and in the brain tissue. These changes may result in the degeneration of neurons and neuron connections. These changes lead to cell damage and eventual death, and reveal themselves through impairment of central nervous system function, including different forms of dementia. Neurodegenerative diseases of the central nervous system that cause different types of dementia are mainly diseases affecting middle-aged to elderly adults.

There are many parallels between different neurodegenerative disorders, including atypical protein assemblies, induced cell death, immune function damage, pro-inflammatory responses and oxidative stress. There is also a growing body of evidence that some acute and chronic infections and inflammation processes are common features of neurodegenerative and neurodevelopmental diseases. For example, infections such as viral and bacterial diseases of the respiratory tract, and a number of other viral, bacterial and fungal pathogenic infections could play a role in the development of these pathologies.

Even though there is still controversy as to how the infections play a role in the progression of neurological diseases, there is evidence of how they may lead to damage in both the infected and neighboring cells. The infection leads to the activation of inflammatory processes and host immune responses, which act as defense mechanisms, and which in turn cause damage to the host's neuronal functions and viability. Neurodegenerative damage due to bacterial and viral pathogens has been reported because of, for example, the production and deposit of misfolded protein aggregates, oxidative stress, deficient autophagic processes, and neuronal death. These effects may act in combination with other factors like aging, metabolic diseases and the genetic makeup of the host to lead to neurodegeneration.

In addition to bacterial and viral infections, many other factors can play a role in the development of these diseases. They include pathological effects caused by heavy metals, nutritional abnormalities, and compromised or damaged immunologic functions and responses; however, practically all neurodegenerative diseases have in common the overexpression of oxidative free radical compounds that cause genetic changes and structural changes in lipids and proteins.

There exist a significant number of etiological and pathogenic similarities between neurological conditions such as, for example, Alzheimer's, Parkinson's and other neurodegenerative diseases. These are: (1) neuronal cell loss, (2) activated microglia and astrocytes, (3) pro-inflammatory state, (4) oxidative stress, and (5) association with many infectious agents.

The ideal treatment plan for neurological conditions coordinates therapies and interventions that meet the specific needs of the individual. Thus, there is a continuing need for new, integrated compositions and methods for treating a broad range of neurological symptoms and improving the overall quality of life and performance for patients diagnosed with neurodegenerative diseases.

BRIEF SUMMARY

The present invention provides compositions and methods for treating and/or preventing neurodegenerative diseases and/or conditions. These conditions may be, for example, Alzheimer's Disease; Parkinson's Disease; Lewy body disease; corticobasal degeneration; corticobasal ganglionic degeneration; multiple system atrophy (MSA); progressive supranuclear palsy (PSP); postencephalitic parkinsonism; Hallervorden-Spatz syndrome; Parkinsonism-dementia complex (PDC) of Guam; Huntington's disease (HD); amyotrophic lateral sclerosis (ALS); multiple sclerosis (MS); prion diseases; prion protein amylo id antipathy; Creutzfeldt-Jakob disease; Gerstmann-Straussler-Scheinker syndrome; Kuru; frontotemporal dementia; Pick's disease; primary progressive aphasia; semantic dementia; Niemann-Pick disease type C; dementia pugilistica (or chronic traumatic encephalophathy (CTE)); Batten disease (or neuronal ceroid lipofuscinosis (NCL)); Friedreich's ataxia; Spinocerebellar ataxia (SCA); Spinal muscular atrophy (SMA); Down's syndrome; Argyrophilic grain disease; non-Guamanian motor neuron disease with NFT; subacute sclerosing panencephalitis (SSPE); and myotonic dystrophy.

In certain embodiments, the compositions and methods of the present invention can be used for treating and/or preventing symptoms and/or comorbidities of these conditions, as well as for reducing the severity and/or delaying the onset of symptoms and/or comorbidities of these conditions.

In specific embodiments, the present invention pertains to the use of a composition comprising a therapeutically-effective amount of a biosurfactant to treat a neurodegenerative disease. In one embodiment, the biosurfactant is the only active ingredient in the composition.

Biosurfactants according to the present invention include low molecular weight glycolipids (e.g., sophorolipids, rhamnolipids, mannosylerythritol lipids and trehalose lipids), lipopeptides (e.g., surfactin, iturin, fengycin and lichenysin), flavolipids, phospholipids (e.g., sphingophospholipids), and high molecular weight polymers such as lipoproteins, lipopolysaccharide-protein complexes, and polysaccharide-protein-fatty acid complexes. The biosurfactants can be in their native form or in any modified or derivative form.

In preferred embodiments, the biosurfactant is isolated and/or purified from the growth medium resulting from fermentation of a biosurfactant-producing microorganism.

The biosurfactant can be used on its own or in combination with other biosurfactants, other active agents and/or drugs for the treatment and/or prevention of neurodegenerative diseases, as well as symptoms and/or comorbidities thereof.

In one embodiment, the microbe-based composition can further comprise carriers, adjuvants, additives, excipients, or other components and/or inactive ingredients as necessary, depending upon, for example, the mode of administration. In one embodiment, the composition can be formulated to be administered via a route of administration, including, for example, oral administration, injection (e.g., intravenous (IV), intramuscular (IM), intraperitoneal, intrathecal or subcutaneous), inhalation, and/or transdermal, rectal, urogenital, ocular, aural, nasal, and/or cutaneous routes, as well as any other form of administration known in the medical arts.

The present invention further provides a method of treating and/or preventing a neurodegenerative disease in a subject, wherein the method comprises administering a therapeutically-effective amount of a microbe-based composition according to the present invention to a subject in need thereof. In a specific embodiment, the method comprises administering a purified biosurfactant to the subject.

In some embodiments, the method comprises diagnosing the subject with a neurodegenerative disease prior to treating the subject according to the present invention.

In some embodiments, the subject has not been diagnosed with a neurodegenerative disease, but has a predisposition for developing a neurodegenerative disease due to, for example, genetics, family history, and/or past trauma or injury. Thus, in one embodiment, the methods can comprise performing genetic testing and/or assessing the subject's family and medical history to determine the likelihood of the subject developing a neurodegenerative disease, prior to administering the composition to the subject.

Advantageously, the materials and methods of the present invention can help improve the quality of life for individuals who are either suffering from a symptom and/or comorbidity of a neurodegenerative disease, or who are currently unaffected by a symptom or comorbidity but wish to prevent the occurrence and/or onset thereof.

DETAILED DISCLOSURE

The subject invention provides compositions and methods for treating neurodegenerative diseases and/or conditions. These diseases may be, for example, Alzheimer's Disease, Parkinson's Disease, and/or others, such as those described elsewhere in this description. The subject invention also provides compositions and methods for treating and/or preventing symptoms and/or comorbidities of these conditions.

In specific embodiments, the subject invention pertains to the use of compositions comprising a biosurfactant to treat a neurodegenerative disease. In one embodiment, the biosurfactant is the only active ingredient in the composition.

In one embodiment, the biosurfactant can be used on its own or in combination with other biosurfactants. In one embodiment, the composition further comprises other active agents and/or drugs for the treatment of these conditions.

Selected Definitions

The term "neurodegeneration" refers to the progressive loss of structure or function of neurons. Neurodegenerative conditions, disorders or diseases are typically incurable, leading ultimately to neuronal death and/or death of the subject. Along with neural degeneration, there are many parallels between different neurodegenerative disorders, including atypical protein assemblies, induced cell death, immune function damage, pro-inflammatory and oxidative stress, as well as infections caused by viruses, bacteria and fungi.

As used herein, the term "treatment" refers to eradicating, reducing, ameliorating, or reversing a sign or symptom of a condition, disease or disorder to any extent, and includes, but does not require, a complete cure of the condition, disease or disorder. Treatment can be curing, improving, or partially ameliorating a disorder. Treatment can be a reduction in the severity of a disorder. Treatment can also include improving or enhancing a condition or characteristic, for example, increasing the function of a particular muscle, tissue or system in the body.

As used herein, "preventing" a condition, disease or disorder refers to avoiding, delaying, forestalling, or minimizing the onset of a condition, disease or disorder. Prevention can, but is not required to be, absolute or complete, meaning the condition, disease or disorder may still develop at a later time and/or with less severity. Prevention can include reducing the severity of the onset of such a condition, disease or disorder, and/or inhibiting the progression of the condition, disease or disorder to a more severe condition or disorder.

The term "comorbidity" as used herein means a disease or condition present simultaneously with another disease or condition. Comorbidities of neurodegenerative diseases and/or conditions include but are not limited to anxiety; attention deficit disorder; brain inflammation; infections; clinical depression; Tourette syndrome; Fragile X syndrome; obsessive-compulsive disorder; bipolar disorder; learning disabilities; sensory disorders; developmental coordination disorder; disorders of the immune system and/or gastrointestinal system, including candidiasis; seizures and/or epilepsy; sleep disorders; increased risk of cancer; dementia; memory loss; language disorders; disorientation; mood swings; loss of motivation; behavioral issues; loss in brain matter; loss in bodily function and/or control; death; and others.

The terms "natural" and "naturally-derived," as used in the context of a chemical compound or substance is a material that is found in nature, meaning that it is produced from earth processes or by a living organism. A natural product can be isolated or purified from its natural source of origin and utilized in, or incorporated into, a variety of applications, including foods, beverages, cosmetics, drugs and supplements. A natural product can also be produced in a lab by chemical synthesis, provided no artificial components or ingredients (i.e., synthetic ingredients that cannot be found naturally as a product of the earth or a living organism) are added.

As used herein, reference to a "microbe-based composition" means a composition that comprises components that were produced as the result of the growth of microorganisms or other cell cultures. A microbe-based composition may comprise the microbes themselves, or the microbes may be separated from the medium in which they were cultivated. The composition can comprise residual cellular components and/or by-products of microbial growth. Preferably, the compositions according to the present invention have been separated from the microbes. The by-products of microbial growth may be, for example, metabolites (e.g., biosurfactants), cell membrane components, expressed proteins, and/or other cellular components.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers and/or appropriate carriers (e.g., water or salt solutions). The microbe-based product may comprise mixtures of microbe-based compositions. The microbe-based product may also comprise one or more components of a microbe-based composition that have been processed in some way such as, but not limited to, filtering, centrifugation, lysing, drying, purification, concentration and the like.

As used herein, an "isolated" or "purified" nucleic acid molecule, polynucleotide, polypeptide, protein, organic compound such as a small molecule (e.g., those described below), or other compound is substantially free of other compounds, such as cellular material, with which it is associated in nature. For example, a purified or isolated biosurfactant is free from the microorganism that produced it as well as the medium in or on which the microorganism grew. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention, e.g., the ability to improve the bioavailability of a substance.

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Target Subjects

The term "subject," as used herein, describes an organism, including mammals, to which treatment with the compositions and compounds according to the present invention can be administered. Mammalian species that can benefit from the disclosed methods of treatment include, but are not limited to, apes, chimpanzees, orangutans, humans, monkeys, and other animals such as dogs, cats, horses, cattle, pigs, sheep, goats, mice, rats, guinea pigs, and hamsters. Preferably, the subject is a human.

The present invention can be useful for treating and/or preventing a neurodegenerative disease, condition or disorder in a subject. The subject can include a person of any age who has been diagnosed with a neurodegenerative disease, condition or disorder.

In one embodiment, the subject is a human diagnosed with dementia or any condition that causes dementia. In one embodiment, the subject is a human diagnosed with Alzheimer's disease (AD). In one embodiment, the subject is a human diagnosed with Parkinson's disease (PD). In one embodiment, the subject is a human diagnosed with another neurodegenerative disease selected from Lewy body disease, corticobasal degeneration, corticobasal ganglionic degeneration, multiple system atrophy (MSA), progressive supranuclear palsy (PSP), postencephalitic parkinsonism, Hallervorden-Spatz syndrome, Parkinsonism-dementia complex (PDC) of Guam, Huntington's disease (HD), amyotrophic lateral sclerosis (ALS), multiple sclerosis (MS), prion diseases, prion protein amyloid antipathy, Creutzfeldt-Jakob disease, Gerstmann-Straussler-Scheinker syndrome, and Kuru, frontotemporal dementia, Pick's disease, primary progressive aphasia, and semantic dementia, Niemann-Pick disease type C, dementia pugilistica (or chronic traumatic encephalopathy (CTE)), Batten disease (or neuronal ceroid lipofuscinosis (NCL)), Friedreich's ataxia, Spinocerebellar ataxia (SCA), Spinal muscular atrophy (SMA), Down's syndrome, Argyrophilic grain disease, non-Guamanian motor neuron disease with NFT, subacute sclerosing panencephalitis (SSPE), and myotonic dystrophy.

In one embodiment, the subject is a person of any age who has not yet been diagnosed with a neurodegenerative disease, but who has a predisposition to the condition due to, e.g., prior injury, family history and/or genetics. Thus, the subject can be a person who wishes to prevent or delay the occurrence of a neurodegenerative disease.

The identification of subjects who are in need of treatment for or prevention of a neurodegenerative disease is well within the knowledge and ability of one skilled in the art. By way of example, a clinician skilled in the art can readily identify, by the use of clinical tests, genetic tests, neurologic and physical examination, and medical/family history, those patients who are suffering from a neurodegenerative disease as well as those who are predisposed to developing a neurodegenerative disease and thus readily determine if an individual is in need of treatment and/or prevention. For instance, neurofibrillary tangles or senile plaques present in neuronal cells and/or cell processes can be determined using electron microscopy (EM) or other clinical techniques known in the art. In addition, spinal fluid or cerebral fluid samples or tissues samples from hippocampal tissue or frontal cortex tissue samples may be obtained from a subject and levels of protein tau present in the samples can be determined using routine techniques such as enzyme-linked immunosorbant assay (ELISA), western blot, and immunological assays.

Treatment of Neurological Disorders, Conditions and/or Diseases

The present invention provides compositions and methods for treating and/or preventing neurodegenerative diseases and/or conditions. The present invention also provides compositions and methods for treating and/or preventing the symptoms and/or comorbidities of these diseases/conditions.

In preferred embodiments, the methods comprise administering a therapeutically-effective amount of a biosurfactant to a subject in need thereof. In one embodiment, the biosurfactant is a purified biosurfactant.

The biosurfactant can be used on its own or in combination with other biosurfactants. In one embodiment, the composition further comprises other active agents and/or drugs for the treatment of neurodegenerative diseases/conditions.

In some embodiments, the method comprises diagnosing the subject with a neurodegenerative disease prior to treating the subject according to the present invention.

In some embodiments, the subject has not been diagnosed with a neurodegenerative disease, but has a predisposition for developing a neurodegenerative disease. Thus, in one embodiment, the methods can comprise performing genetic testing and/or assessing the subject's family and medical history to determine the likelihood of the subject developing a neurodegenerative disease, prior to administering the composition to the subject.

The present invention can be useful for the treatment and/or prevention of a neurodegenerative disease, condition or disorder, as well as the symptoms and/or comorbidities thereof. Target diseases, conditions and/or disorders include those that cause dementia and/or decreased neurological function, particularly in the brain.

The term "dementia" as used herein, refers to a decline in mental ability that is severe enough to interfere with a subject's daily life. Dementia is a symptom and/or comorbidity of a broad category of diseases, such as the neurodegenerative diseases described elsewhere in this description, that cause a long term decrease in the ability of a subject to think clearly and to remember. Dementia can also be caused by certain vitamin or nutrient deficiencies, brain injury, cancer, anoxia, normal-pressure hydrocephalus, subdural hematomas, syphilis, metabolic abnormalities, and reactions to certain medications.

In one embodiment, the present invention provides compositions and methods for treating the symptoms and/or comorbidities of Alzheimer's Disease (AD).

AD is a chronic neurodegenerative disease that is the cause of 60-70% of dementia cases. The symptoms usually start slowly and worsen over time. In AD, pathological changes in the brain tissues and cells occur as a result of abnormal deposition of the amyloid β (Aβ) peptide in the brain, and intracellular accumulation of neurofibrillary tangles of tau protein. Symptoms of AD include short-term memory loss, problems with language, disorientation (including easily getting lost), mood swings, loss of motivation, decrease in self-care, and behavioral issues. As a person's condition declines, they often withdraw from family and society. Gradually, bodily functions are lost, ultimately leading to death.

The neurotoxic Aβ peptide together with r protein are mediators of the neurodegeneration that is among the main causative factors of Alzheimer's; however, these factors are mainly triggered and promoted by oxidative stress. Oxidative stress occurs because of increased production of free radicals. Increased production of potent free radicals initially yields the superoxide radical that converts into hydrogen peroxide. Then, highly reactive hydroxyl radicals (reactive oxygen species or ROS) are produced. ROS can react with lipids, proteins, nucleic acids, and other molecules that are capable of altering their structures and functions. It further results in damage to various tissues and organs, including the brain.

Moreover, all genetic defects seen in patients with AD are not necessarily inherited by nature. Some may be caused by the action of ROS. Some may also be caused by direct actions of bacterial, viral, fungal and parasitic infections, or by indirect effects resulting from these infections, such as inflammatory responses, excessive oxidative stress, and increased production of ROS.

Increasing evidence suggests that in the course of AD pathogenesis, not only is the brain's neuronal compartment damaged, but the damage also involves the process of immunological interactions in the brain. Misfolded and aggregated proteins bind to pattern recognition receptors on glial cells and trigger a strong innate immune response characterized by release of inflammatory mediators, which contribute to disease progression and severity. Genomic analysis shows that several genes that can play a role in increasing the risk for sporadic AD encode factors that regulate glial clearance of misfolded proteins and the inflammatory reaction. External factors, including: systemic inflammation, obesity, and perverted immune system's function and response, are likely to interfere with immunological processes of the brain and further promote disease progression.

Certain infections may be linked to AD, though there is likely no single pathogen responsible for initiation/promotion of the disease. Emerging evidence supports the hypothesis of the role of neurotropic viruses from the Herpesviridae family, especially human herpesvirus 1 (herpes simplex 1 or HSV-1), cytomegalovirus (CMV), and human herpesvirus 2 (herpes simplex 2 or HSV-2), in AD neuropathology. HSV-1 is thought to be involved in the abnormal aggregation of beta amyloid fragments within the AD brain by reducing the amount of full-length beta amyloid precursor protein and increasing the amounts of their fragments. HSV-1 infection of glial and neuronal cells results in a dramatic increase in the intracellular levels of beta amyloid forms, whereas the levels of native beta amyloid precursor protein are decreased. It is most likely that HSV-1 is involved directly in the development of senile-associated plaques.

Amongst bacteria, special attention is focused on spirochetes family, and on periodontal pathogens such as *Porphyromonas gingivalis* or *Treponema denticola* that could cause chronic periodontitis and possibly contribute to the clinical onset of AD. *Chlamydophila pneumoniae* is another pathogen that has attracted considerable attention. This intracellular bacterium has a tropism for neural tissue, and it has been found at high incidence in the brains of AD patients. *C. pneumoniae* can invade endothelial cells and promote the transmigration of monocytes through human brain endothelial cells into the brain parenchyma.

Some AD patients also have other bacterial infections, such as *Borrelia burgdorferi*, a causative agent of lyme disease infection. This pathogen could be a primary agent in the formation of AD beta amyloid plaques. Multiple reports indicate that AD nerve cells are often positive for *B. burgdorferi*, indicating that this intracellular bacterium could be important in the pathogenesis of AD.

In one embodiment, the present invention provides compositions and methods for treating the symptoms and/or comorbidities of Parkinson's Disease (PD).

PD is a progressive, chronic neurodegenerative disorder characterized by akinesia, muscular rigidity and resting tremor. In addition, autonomic dysfunction, olfactory disturbances, depression, sensory and sleep disturbances, and dementia are symptoms of Parkinson's. Subjects with this condition experience a partial loss of the dopaminergic neurons in the substantia nigra pars compacta and the degeneration of some nerve fibers in the striatum, together with the presence of Lewy bodies and alpha-synuclein. More extensive brain degeneration also occurs from the medulla oblongata to the cerebral cortex.

The cause of nigral dopaminergic neuronal cell death in PD and its underlying mechanisms remain largely unknown; however, inflammatory events are involved, because inflammatory features have been described in the brain of PD patients. Age-related inclusion bodies and protein aggregations or defects in their degradation characteristically occur in PD, but their role in PD pathogenesis remains unclear. Some evidence suggests a relationship between PD and specific genetic changes, such as changes in the genes affecting mitochondria, protein degradation, organelle trafficking and vesicular fusion, and in proteins involved in oxidative stress or antioxidant function.

The pathogenesis of PD has been proposed to be due to multiple genetic and neurotoxic events that produce oxidative damage and cell death. In the case of PD, the relevant targets of toxic events are neuromelanin-containing dopaminergic neurons of the substantia nigra. In addition to genetic background, multiple environmental factors, such as long-term toxic exposures and trauma early in life, are prominent risk factors for PD. For example, early life exposure to brain injury, chemicals, and/or infections may initiate a cyclic inflammatory process involving oxidative damage, excitotoxicity, mitochondrial dysfunction, and altered proteolysis that later in life results in substantia nigra neuron death.

Because there is currently no therapy that delays the neurodegenerative process, modification of the disease course by neuroprotective therapy is an important unmet clinical need. Increasing evidence suggests that oxidative stress plays a major role. The metabolism of dopamine contributes to oxidative stress, resulting in modification of intracellular macromolecules whose functions are important for cell survival. Mitochondrial dysfunction and the consequent increase in reactive oxygen species also trigger a sequence of events that leads to cell demise. In addition, activated microglia produce nitric oxide and superoxide during neuroinflammatory responses, and this is aggravated by the molecules released by damaged dopaminergic neurons such as α-synuclein, neuromelanin and matrix metalloproteinase-3.

Some evidence also suggests that there is a possible deleterious effect of neuroinflammatory processes caused by chronic infections in PD patients. One infection found in PD that has aroused considerable interest is the presence of chronic gastrointestinal *Helicobacter pylori*. It was shown that treatment of this infection offers relief to late stage cachexia in PD patients receiving L-dopa. *H pylori*-infected PD patients showed reduced L-dopa absorption and increased clinical disability, whereas treatment of this infection increased L-dopa absorption and decreased clinical disability. *H pylori* may not be directly involved in the pathogenesis of PD, but its systemic presence could affect the progression of PD, probably by stimulating inflammation and autoimmunity.

Some other chronic infections in PD have been linked to inflammation and autoimmune responses. Experimental models of PD have been developed using neurological viral or bacterial infections to initiate the pathogenic process. Spirochetes have been found in Lewy bodies of PD patients. Infections, such as: herpes simplex virus, Epstein-Barr virus, cytomegalovirus, varicella zoster virus, influenza virus A, coxsackie virus, echo virus, some opportunistic infections of the basal ganglia, coronavirus, and other infections, have been found in PD and could be important in stimulating inflammation and autoimmune responses.

In one embodiment, the present invention provides compositions and methods for treating the symptoms and/or comorbidities of a Parkinsonian disease or a disease that can lead to Parkinsonism, including Lewy body disease, corticobasal degeneration, corticobasal ganglionic degeneration, multiple system atrophy (MSA), progressive supranuclear palsy (PSP), postencephalitic parkinsonism, Hallervorden-Spatz syndrome, and Parkinsonism-dementia complex (PDC) of Guam.

In one embodiment, the present invention provides compositions and methods for treating the symptoms and/or comorbidities of a neurodegenerative disease selected from Huntington's disease (HD); amyotrophic lateral sclerosis (ALS); multiple sclerosis (MS); prion diseases, such as prion protein amyloid antipathy, Creutzfeldt-Jakob disease, Gerstmann-Straussler-Scheinker syndrome, and Kuru; frontotemporal dementia, including Pick's disease, primary progressive aphasia, and semantic dementia; Niemann-Pick disease type C; dementia pugilistica (or chronic traumatic encephalopathy (CTE)); Batten disease (or neuronal ceroid lipofuscinosis (NCL)); Friedreich's ataxia; Spinocerebellar ataxia (SCA); Spinal muscular atrophy (SMA); Down's syndrome; Argyrophilic grain disease; non-Guamanian motor neuron disease with NFT; subacute sclerosing panencephalitis (SSPE); and myotonic dystrophy.

In one embodiment, the present invention provides compositions and methods for treating and/or preventing the symptoms and/or comorbidities of more than one neurodegenerative disease.

Compositions

In one embodiment, the present composition is a microbe-based composition comprising a biosurfactant. In one embodiment, the biosurfactant is the only active ingredient in the composition.

The biosurfactant can be used on its own or in combination with other biosurfactants. In one embodiment, the composition further comprises other chemicals, active agents and/or pharmaceutical drugs. In one embodiment, the composition can further comprise naturally-derived substances with therapeutic properties, such as herbal supplements and/or extracts.

The biosurfactants useful according to the subject invention are naturally-derived, safe, biodegradable and can be produced with ease at low cost using selected organisms in or on renewable substrates.

Biosurfactants are compounds of a microbial origin (metabolic by-products of bacteria, yeasts and filamentous fungi) that exhibit surfactant properties (emulsification capabilities and a reduction in surface/interfacial tension). They are commonly classified based on their biochemical nature and/or by the species of microbe that produces them.

Biosurfactants according to the present invention include low molecular weight glycolipids (e.g., sophorolipids, rhamnolipids, mannosylerythritol lipids and trehalose lipids), lipopeptides (e.g., surfactin, iturin, fengycin and lichenysin), flavolipids, phospholipids (e.g., sphingophospholipids), and high molecular weight polymers such as lipoproteins, lipopolysaccharide-protein complexes, and polysaccharide-protein-fatty acid complexes.

With glycolipids, the degree of polarity of the molecule depends on the hydrocarbons used as a substrate. Typical examples of glycolipids are rhamnolipids produced by, e.g., *Pseudomonas* spp., sophorolipids produced by e.g., *Candida* spp., *Starmerella bombicola* and *Wickerhamomyces anomalus*, trehalose lipids produced by *Rhodococcus* sp. and mannosylerythritol lipids produced by *Pseudozyma* spp. Lipopeptides include surfactin, which is one of the most potent biosurfactants reported in the literature, pumilacidin, iturin, fengycin and lichenysin, and can be produced by *Bacillus* spp. bacteria (e.g., *B. subtilis*). Phospholipids include biosurfactants produced by some *Corynebacterium* and *Acinetobacter*.

All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces. Furthermore, biosurfactants accumulate at interfaces, and reduce the surface and interfacial tension between the molecules of liquids, solids, and gases, thus leading to the formation of aggregated micellular structures in solution.

Most biosurfactant-producing organisms produce biosurfactants in response to the presence of a hydrocarbon source (e.g., oils, sugar, glycerol, etc.) in the growing media. Other media components such as concentration of iron can also affect biosurfactant production significantly. Microbial biosurfactants are produced by a variety of microorganisms, such as, for example, *Pseudomonas* spp. (*P. aeruginosa, P. putida, P. florescens, P. fragi, P. syringae*); *Flavobacterium* spp.; *Bacillus* spp. (*B. subtilis, B. pumillus, B. licheniformis, B. amyloliquefaciens, B. cereus*); *Wickerhamomyces* spp. (e.g, *W. anomalus*), *Candida* spp. (e.g., *C. albicans, C. rugosa, C. tropicalis, C. lipolytica, C. torulopsis*); *Rhodococcus* spp.; *Arthrobacter* spp.; *Campylobacter* spp.; *Corynebacterium* spp.; *Pichia* spp. (e.g., *P. anomala, P. guilliermondii, P. occidentalis*); *Starmerella* spp. (e.g., *S. bombicola*); and so on.

The biosurfactants may be obtained by fermentation processes known in the art, e.g., solid-state fermentation, submerged fermentation, or modifications, hybrids and/or combinations thereof. The production of biosurfactants with the use of renewable substrates and different microbial species, as well as the variation in culture parameters (incubation time, stirring speed, pH of the medium and added nutrients), allow for the acquisition of compounds with distinct structural and physical properties. This makes it possible to produce a wide variety of compounds that can elicit different physical, chemical, biochemical and biophysical properties.

The biosurfactant produced by microorganisms of interest may be retained in the microorganisms or secreted into their growth medium. The growth medium may contain compounds that stabilize the activity of the biosurfactant.

In certain embodiments, the biosurfactant is isolated and/or purified from the growth medium resulting from fermentation of a biosurfactant-producing microorganism. The biosurfactant can be further concentrated, if desired.

The biosurfactant can be utilized in any of its structural forms, including derivatives, fractions, conformations, isoforms, subtypes, including forms that are naturally or artificially (or chemically) modified. The use of different isomers or forms of biosurfactants is beneficial in that the skilled artisan can tailor the composition depending upon, for example, its effectiveness for treating a particular disease or its interactions with a particular pharmaceutical compound. That is, certain isoforms of a biosurfactant might be more effective with certain drugs due to, for example, the chemical structure of the compound.

In certain embodiments, the biosurfactant is a sophorolipid (SLP), such as, for example, a lactonic or acidic form sophorolipid, a non-acetylated sophorolipid, a mono-acetylated sophorolipid, a di-acetylated sophorolipid, or any other isoform thereof.

In certain embodiments, the biosurfactant is a rhamnolipid (RLP), such as, for example, a mono-rhamnolipid, a di-rhamnolipid, or any other isoform thereof.

In certain embodiments, the biosurfactant is a mannosylerythritol lipid (MEL), such as, for example, MEL-A, MEL-B, MEL-C, or MEL-D, or any other isoforms with varying fatty acid lengths and/or hydrophobic portions.

In certain embodiments, the biosurfactant is a trehalose lipid (TL), including any form thereof.

In certain embodiments, the biosurfactant is a lipopeptide, including linear or cyclic form lipopeptides, or any other isoforms thereof. As an example, surfactin is a lipopeptide that can have a structure comprising a peptide loop of seven amino acids and a hydrophobic fatty acid chain thirteen to fifteen carbons long. In an exemplary embodiment, the amino acids comprise L-aspartic acid, L-leucine, glutamic acid, L-leucine, L-valine and two D-leucines.

As another example, iturin is a lipopeptide with a structure comprising a peptide loop of seven amino acids and a β-amino fatty acid chain that can vary from 14 to 17 carbons long. In one embodiment, iturin A is utilized according to the subject invention.

In one embodiment, the biosurfactants of the present microbe-based composition have a low critical micelle concentrations (CMC), which means that they are effective at low concentrations, e.g., below minimal toxic concentrations.

In one embodiment, the biosurfactants of the present microbe-based composition are anti-inflammatory due to suppression of increased expression of IFN-γ, IL-6, iNOS, nitric oxide and downregulation of the LPS-induced TLR4 protein expression of macrophages.

In one embodiment, the biosurfactants of the present microbe-based composition can modulate the immune system function and response by increasing production of cytokines and other mediators to establish a more anti-inflammatory state; suppressing T cells proliferation with down-regulation of amounts of activated CD8(+) T cells (which produce TNF-α and IFN-γ); increasing CD4(+) CD25(+) regulator T cells (Tregs); and increasing IL-10 switching of the immune response from Th1- to Th2-type.

In one embodiment, the biosurfactants of the present microbe-based composition can form pores in membranes to improve penetration into cells, tissues and organs. For example, in one embodiment, the biosurfactants can help detach the tight junctions of the gastrointestinal system, thus allowing for enhanced drug absorption through epithelial barriers and the blood-brain barrier.

In one embodiment, the biosurfactants of the present microbe-based composition can suppress ROS to reduce damage caused by overproduction thereof.

In one embodiment, the biosurfactants of the present microbe-based composition can inhibit P-glycoprotein, a cellular transporter which acts as a physiological barrier by extruding exogenous substances out of cells. This effect can help biosurfactants penetrate the blood-brain barrier, prevent P-glycoprotein-mediated drug efflux and assist any substrate molecules (e.g., pharmaceutical drugs) in reaching and/or having a desired effect on the central nervous system.

In one embodiment, the biosurfactants of the present microbe-based composition have significant antibacterial, antiviral and antifungal properties without being classified as antibiotics or antivirals.

Biosurfactants can be delivered to a subject in many different forms. Illustrative examples of the delivery forms include intravenous, intra-arterial, and intraperitoneal administration.

The biosurfactants are preferably present in the composition in therapeutically-effective amounts. In one embodiment, this means the biosurfactants are present at or above the critical micelle concentration (CMC). CMC is the concentration of surfactants above which micelles will form and all additional surfactants added to the system either convert to micelles or add to the existing micelles.

In some cases, a biosurfactant has some non-specific toxicity and can lyse animal cells as well as pathogen cells when used at certain levels. In one embodiment, the concentration of biosurfactant used according to the present invention is at or above the CMC, but below a concentration that causes chronic toxicity. Preferably, in one embodiment, the amount of biosurfactant is about 5 to 10 times lower than the concentration causing chronic toxicity upon daily administration to a subject. These concentrations can vary depending upon, for example, the biosurfactant used.

In certain embodiments, a therapeutically-effective amount of biosurfactant in the composition is 0.001 to 90% by weight (wt %), preferably 50% or less, 25% or less, even more preferably, 10% or less, 5% or less, or 1% or less. In certain embodiments, the biosurfactant concentration is about 0.001 to 1%, 0.01% to 0.8%, or 0.1% to 0.5%.

In some embodiments, the composition further comprises a therapeutically-effective dose of an additional active ingredient, chemical and/or pharmaceutical compound.

In certain embodiments, pharmaceutical compounds can include those typically used for treating the symptoms and/or comorbidities of neurodegenerative diseases, for example, levodopa, tacrine, donepezil, rivastigmine, galanthamine, memantine, riluzole, edaravone, tetrabenazine, haloperidol, cimetidine, risperidone, quetiapine, amantadine, levetiracetam, clonazepam, beta interferons, ocrelizumab, glatiramer acetate, dimethyl fumarate, fingolimod, teriflunomide, natalizumab, alemtuzumab, and others such as dopamine agonists, MAO inhibitors, anticholinergic agents, cholinesterase inhibitors, antipsychotic drugs, steroids, corticosteroids, muscle relaxants, antidepressants, SSRIs and anti-inflammatory compounds.

Naturally-derived substances that have been used for promoting cognitive health can also be included, such as, for example, resveratrol, ginger, curcumin, turmeric, liquorice, *ginseng*, sage, rosemary, ginkgo, chamomile, willow bark, stinging nettle, maca, lemon, saffron and kava.

In some embodiments, the composition further comprises additional carriers, adjuvants, excipients, and/or other inactive ingredients.

Formulation and Methods of Administration

The dosage and the frequency of administration of the microbe-based composition may vary depending on the following factors: the severity of the disease to be treated, the route of administration, and the age, physical condition and response of the subject to be treated. In one embodiment, the biosurfactant is administered daily to the subject.

Compositions according to the subject invention may comprise, in addition to active ingredients, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

The compounds and compositions of the present invention can be administered to the subject being treated in a single dose or in several doses by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject. In a one embodiment, the compounds and compositions of the subject invention are administered orally.

In one embodiment, the composition can be formulated as an orally deliverable substance and delivered in the form of an orally consumable product. An "orally deliverable substance" is any physiologically active substance delivered via initial absorption into the gastrointestinal tract, or into the mucus membranes of the mouth (e.g., by way of sublingual or buccal administration).

Orally consumable products according to the invention are any preparations or compositions suitable for consumption, for nutrition, for oral hygiene or for pleasure, and are products intended to be introduced into the human or animal oral cavity, to remain there for a certain period of time and then to either be swallowed (e.g., food ready for consumption or pills) or to be removed from the oral cavity again (e.g., chewing gums or products of oral hygiene or medical mouth washes).

Orally consumable products include all substances or products intended to be ingested by humans or animals in a processed, semi-processed or unprocessed state. This also includes substances that are added to orally-consumable products (particularly food and pharmaceutical products) during their production, treatment or processing and intended to be introduced into the human or animal oral cavity.

Orally-consumable products can also include substances intended to be swallowed by humans or animals and then digested in an unmodified, prepared or processed state; the orally consumable products according to the invention therefore also include casings, coatings or other encapsulations that are intended also to be swallowed together with the product or for which swallowing is to be anticipated.

In one embodiment, the orally-consumable product is a capsule, pill, syrup, emulsion or liquid suspension containing a desired orally-deliverable substance. In one embodiment, the orally-consumable product can comprise an orally-deliverable substance in powder form, which can be mixed with water or another liquid to produce a drinkable orally-consumable product.

In some embodiments, the orally-consumable product according to the invention can comprise one or more formulations intended for nutrition or pleasure. These particularly include baking products (e.g., bread, dry biscuits, cake, and other pastries), sweets (e.g., chocolates, chocolate bar products, other bar products, fruit gum, coated tablets, hard caramels, toffees and caramels, and chewing gum), alcoholic or non-alcoholic beverages (e.g., cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, and fruit or vegetable juice preparations), instant beverages (e.g., instant cocoa beverages, instant tea beverages, and instant coffee beverages), meat products (e.g., ham, fresh sausage preparations or raw sausage preparations, and seasoned order, marinated fresh meat or salted meat products), eggs or egg products (e.g., dried whole egg, egg white, and egg yolk), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, whey, butter, buttermilk, and partly or wholly hydrolyzed products containing milk proteins), products from soy protein or other soy bean fractions (e.g., soy milk and products prepared thereof, beverages containing isolated or enzymatically treated soy protein, soy flour containing beverages, preparations containing soy lecithin, fermented products such as tofu or tempeh products prepared thereof and mixtures with fruit preparations and, optionally, flavoring substances), fruit preparations (e.g., jams, fruit ice cream, fruit sauces, and fruit fillings), vegetable preparations (e.g., ketchup, sauces, dried vegetables, deep-freeze vegetables, pre-cooked vegetables, and boiled vegetables), snack articles (e.g., baked or fried potato chips (crisps) or potato dough products, and extrudates on the basis of maize or peanuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening or whitening beverages or other food). The present compositions may also serve as semi-finished products for the production of other compositions intended for nutrition or pleasure.

The compositions described herein can also contain acceptable additives as will be understood by one skilled in the art, depending on the particular form of the delivery method. Non-limiting examples of such additives include suspending agents, emulsifying agents, non-aqueous vehicles, preservatives, buffer salts, flavoring, coloring, and sweetening agents as appropriate. Non-limiting examples of specific additives include: gelatin, glycerin, water, beeswax, lecithin, cocoa, caramel, titanium dioxide, and carmine. Preparations can be suitably formulated to give controlled release of the ingredients.

The composition can additionally comprise a pharmaceutically acceptable carrier widely employed in the art of drug-manufacturing. In some cases, the pharmaceutically acceptable carrier is a carrier suitable for administration to a human subject or other mammal including, without limitation, sterile aqueous or non-aqueous solutions, suspensions, and emulsions. The pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, liposomes, and the like. Examples of non-aqueous solvents include, without limitation, propylene glycol, polyethylene glycol, vegetable oils, and injectable organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration.

For intravenous, cutaneous or subcutaneous injection, or injection at the site of affliction, the composition can be formulated as a parenterally acceptable aqueous solution with suitable pH, isotonicity and stability. Those of relevant skill in the art are well able to prepare suitable solutions using, for example, isotonic vehicles such as sodium chloride injection, ringer's injection, lactated ringer's injection. Preservatives, stabilizers, buffers, antioxidants and/or other additives may be included, as required.

For oral administration, tablets or capsules can be prepared by conventional means with acceptable excipients, such as binding agents, fillers, lubricants, disintegrants, or wetting agents. The tablets can be coated and may comprise a solid carrier such as gelatin or an adjuvant. Liquid compositions generally comprise a liquid carrier such as water, petroleum, animal or vegetable oils, mineral oil or synthetic oil. Liquid preparations for oral administration can take the form of, for example, solutions, syrups, or suspension, or they can be presented as a dry product for constitution with saline or other suitable liquid vehicle before use. Physiological saline solution, dextrose or other saccharide solution or glycols such as ethylene glycol, propylene glycol or polyethylene glycol may be included.

The choice and amount of the aforesaid agents are within the expertise and the routine skills of those skilled in the art.

In one embodiment, the adjuvant composition is formulated as a delivery system for a pharmaceutical drug, wherein the biosurfactants form a liposome or nanocapsule with the drug encapsulated therein. In one embodiment, additional biological polymers can be included to provide further structure for the nanocapsule.

This nanocapsule delivery system can enhance the bioavailability of a drug compound by protecting the compound from components in the blood, such as proteins and other molecules, that otherwise might bind to the compound and prevent it from penetrating a target site. Additionally, the nanocapsule delivery system can allow for drug that might otherwise by degraded by acids or enzymes in the GI tract to be administered orally, as it creates a barrier against the acids or enzymes. Furthermore, the nanocapsule delivery system formulation allows for time release of the drug, thereby reducing the potential toxicity or potential negative side-effects of a compound in a subject The terms "therapeutically effective amount," "effective amount," and "effective dose" are used in this disclosure to refer to an amount of a compound or composition that, when administered to a subject, is capable of reducing a symptom of a disease, condition or disorder in a subject. For example, the effective amount of the compounds and compositions of the present invention is an amount capable of reducing levels of, for example, protein tau in a subject. In certain embodiments, the effective amount enables a 5%, 25%, 50%, 75%, 90%, 95%, 99% and 100% reduction of levels of protein tau (e.g. soluble protein tau intermediates and/or aberrant protein tau) in a subject.

The actual amount will vary depending on a number of factors including, but not limited to, the particular disorder being treated, the severity of the disorder, the size and health of the patient, and the route of administration. A skilled medical practitioner can readily determine the appropriate amount using methods known in the medical arts.

As used herein, "reduction" refers to a negative alteration, and the term "increase" refers to a positive alteration, wherein the negative or positive alteration is at least 0.25%, 0.5%, 1%, 5%, 10%, 15%, 20%, 25%, 30%, 35%, 40%, 45%, 50%, 55%, 60%, 70%, 75%, 80%, 85%, 90%, 95%, or 100%.

Illustratively, dosage levels of the administered active ingredients can be: orally, 0.01 to about 500 mg/kg of body weight; intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; intranasal instillation, 0.01 to about 20 mg/kg; and aerosol, 0.01 to about 20 mg/kg.

In some cases, a biosurfactant has some non-specific toxicity and can lyse animal cells as well as pathogen cells when used at certain levels. For example, certain biosurfactants, such as SLP and surfactin, can have hemolytic effects at certain concentrations, and thus, use of intravascular administration should be performed with caution. In certain embodiments, to prevent the possibility of toxicity, the biosurfactants are administered to the subject orally.

In one exemplary embodiment, the biosurfactant is a sophorolipid (SLP). SLP can be administered orally at doses of, for example, 5 grams/kg of body weight or less without toxicity. For daily administration, the preferred dose of SLP is about 100 to 500 mg/kg of body weight per day. In one embodiment, the daily dose of other glycolipids, such as rhamnolipids, mannosylerythritol lipids and trehalose lipids is about 300 to 500 mg/kg of body weight.

In one exemplary embodiment, the biosurfactant is a surfactin. Intravascular administration of surfactin at concentrations of about 40 µM to 60 µM can produce toxic effects. However, surfactin can be administered at concentrations of, for example, 25 µM or below without producing any significant toxic effects. In one embodiment, the dosage of surfactin or other lipopeptides is about 1 to 50 mg/kg of body weight per day.

Once improvement of the subject's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Subjects may however require intermittent treatment on a long-term basis upon any recurrence of disease symptoms.

In addition, in vitro assays may optionally be employed to help identify optimal dosage ranges. The precise dose to be employed in the formulation/composition will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

The compounds and compositions of the present invention can be used to treat and/or prevent neurodegenerative diseases including, but not limited to, Alzheimer's disease, Parkinson's disease, Lewy body disease, corticobasal degeneration, corticobasal ganglionic degeneration, multiple system atrophy (MSA), progressive supranuclear palsy (PSP), postencephalitic parkinsonism, Hallervorden-Spatz syndrome, Parkinsonism-dementia complex (PDC) of Guam; Huntington's disease (HD); amyotrophic lateral sclerosis (ALS); multiple sclerosis (MS); prion diseases, such as prion protein amyloid antipathy, Creutzfeldt-Jakob disease, Gerstmann-Straussler-Scheinker syndrome, and Kuru; frontotemporal dementia, including Pick's disease, primary progressive aphasia, and semantic dementia; Niemann-Pick disease type C; dementia pugilistica (or chronic traumatic encephalopathy (CTE)); Batten disease (or neuronal ceroid lipofuscinosis (NCL)); Friedreich's ataxia; Spinocerebellar ataxia (SCA); Spinal muscular atrophy (SMA); Down's syndrome; Argyrophilic grain disease; non-Guamanian motor neuron disease with NFT; subacute sclerosing panencephalitis (SSPE); myotonic dystrophy, and/or treat or prevent the symptoms and/or comorbidities of any of these conditions.

We claim:

1. A method for treating a neurodegenerative disease and a comorbidity, wherein said method comprises administering to a subject in need of such treatment an effective amount of a mannosylerythritol lipid (MEL), wherein said neurodegenerative disease is Alzheimer's disease, Parkinson's disease, amyotrophic lateral sclerosis (ALS), or multiple sclerosis (MS), and said comorbidity is a microbial infection.

2. The method according to claim 1, wherein said MEL is the only active ingredient administered to the subject.

3. The method according to claim 1, wherein said MEL is administered to the subject via a route of administration that is oral, inhalation, parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intracisternal injection, infusion, and/or electroporation.

4. The method according to claim 3, wherein said MEL is administered to the subject orally.

5. The method according to claim 1, wherein said MEL is administered with a biosurfactant other than MEL.

6. The method according to claim 1, wherein the amount of said MEL is at or above critical micelle concentration (CMC) but below chronic toxicity concentration.

7. The method according to claim 6, wherein the amount of said MEL is 0.1 to 500 mg/kg of the subject's body weight.

8. The method according to claim 7, wherein the amount of said MEL is 1 to 50 mg/kg of the subject's body weight.

9. The method according to claim 1, wherein said MEL is administered to the subject once daily.

10. The method according to claim 1, wherein said MEL comprises MEL-C and/or MEL-D.

11. The method according to claim 1, wherein said microbial infection is caused by herpes simplex virus, Epstein-Barr virus, cytomegalovirus, varicella zoster virus, influenza virus A, coxsackie virus, echo virus, or coronavirus.

12. A method of treating amyotrophic lateral sclerosis, wherein said method comprises administering to a subject in need of such treatment an effective amount of at least two biosurfactants selected from the group consisting of a sophorolipid, a rhamnolipid, and a mannosylerythritol lipid.

* * * * *